US005356398A

United States Patent [19]

Willis

[11] Patent Number: 5,356,398

[45] Date of Patent: Oct. 18, 1994

[54] DISPOSABLE BAG FOR THE COLLECTION OF BODY FLUIDS

[75] Inventor: Michael W. Willis, Riverton, Utah

[73] Assignee: Laser Corporation, Salt Lake City, Utah

[21] Appl. No.: 92,716

[22] Filed: Jul. 16, 1993

[51] Int. Cl.[5] .............................................. A61M 1/00

[52] U.S. Cl. .................................... 604/321; 128/760; 383/63

[58] Field of Search ................ 128/760; 604/317, 321, 604/333, 355; 383/9, 34, 36, 49, 61, 63, 65, 69

[56] References Cited

U.S. PATENT DOCUMENTS

Re. 34,117 10/1992 Martin et al. ......................... 383/63
3,797,734 3/1974 Fleury et al. ....................... 128/760
4,657,792 4/1987 Ausnit .................................. 383/63
4,990,145 2/1991 Fleury ................................ 604/317
5,067,882 11/1991 Wirth et al. .......................... 383/63
5,116,139 5/1992 Young et al. ......................... 383/63
5,211,481 5/1993 Tilman ................................. 383/63

FOREIGN PATENT DOCUMENTS 139412 5/1985 European Pat. Off. .............. 383/63

*Primary Examiner*—Randall L. Green
*Assistant Examiner*—Rob Clarke
*Attorney, Agent, or Firm*—Olive & Olive

[57] ABSTRACT

The present invention provides a disposable bag for the collection of body fluids with an improved sealing structure. The disposable bag comprises a flexible collection bag having a pair of seal strips adjacent its open end. A resiliently flexible funnel is sealing attached within the open end of the bag in a position to not interfere with the seal strips and a flexible non-return valve is sealed to the bottom of the funnel. A gauge indicating the volume of fluid collected and a label portion for identification are provided on a side of the bag.

2 Claims, 2 Drawing Sheets

DISPOSABLE BAG FOR THE COLLECTION OF BODY FLUIDS

BACKGROUND OF THE INVENTION

1. Field of the Invention

This invention relates to disposable bags, and in particular to disposable bags for the collection and monitoring of body fluids.

2. Description of the Related Art

It is a common procedure in the field of medicine to collect and monitor the volume of fluids entering and exiting the body of a sick patient. The fluid collection and volume measurement may be done to evaluate the patient's progress toward better health or to assure that the patient maintains an acceptable fluid balance between intake and discharge.

In many illnesses, the patient will periodically vomit, thereby discharging a quantity of fluid from the body. The complete control and measurement of bodily fluid balance requires that this vomit be included for analysis with the other body fluids, such a urine. The bag of the present invention is adapted to the collection of either vomit or urine.

In addition to monitoring fluid volume, it is important to securely contain any vomit or urine of a sick patient in order to minimize contamination and spread of disease. Therefore, there is a need to effectively seal the container once the fluid has been collected.

A further use of a disposable bag for the collection of vomit occurs in airplanes where motion sickness may induce regurgitation. While some of the requirements relating to sick patients do not apply to airplane passenger use, it is nonetheless important to collect any vomit as neatly as possible and to seal the collecting bag to prevent spillage in a moving airplane.

Fluid collecting bags have been disclosed, for example in U.S. Pat. No. 3,797,734 to Fluery et al. for DISPOSABLE BAGS and U.S. Pat, No. 4,990,145 to Fluery for DISPOSABLE BAG WITH HAND PROTECTION, the teachings of which are incorporated herein by reference. Both of these patents teach a disposable bag having a manually openable funnel at the top and an internal "duck-bill" type valve within the bag. In addition, a fluid collection bag (hereinafter referred to as the EMS bag) of design similar to the patent teachings and including a printed scale for the measurement of fluid volume is supplied by E.M.S. Alliance of Richmond, Calif. In all these prior art bag constructions, the entry funnel protrudes above the upper extremity of the bag. The "duck-bill" valve is depended upon as the principal means for sealing the bag's contents. In addition, score lines below the upper edge of the funnel permit upper portions of the funnel to be folded in overlapping relation for additional protection against spillage. However, the folded portions of the funnel do not form a leak proof seal and at best prevent large particles form being sloshed out of the bag.

The primary drawback of each of the know fluid collection bag designs is that the sealing means is insufficient either to prevent disease spread or spills in case of dropping or inverting the filled bag. In order to properly seal the existing bags, it is necessary to either tape the funnel closed after use or insert the filled bag into another container. A second shortcoming relating to the hospital setting is that in order to identify the contents of the bag for record keeping purpose, one must attach a tag or label, since no provision is made for writing on the type of bag in current use.

It is therefore an object of this invention to provide a bag for the collection body fluids with integral and substantially improved sealing means.

It is a further object of the invention to provide a bag for the collection of body fluids and constructed so as to permit written information to be applied to the bag itself thereby eliminating the, need for a separate, tag or label.

Other objects and advantages will be more fully apparent from the following disclosure and appended claims.

SUMMARY OF THE INVENTION

The present invention comprises a plastic bag for the collection of body fluids having a paperboard formed internally mounted funnel at its upper end with associated resiliently flexible, funnel structure enabling the funnel to be manually opened and closed. The upper extremity of the funnel is sealed to the inner wall of the bag in a position which causes the upper extremity of the funnel to reside below a pair of closure lips formed at the top of the bag. The closure lips located on the upper edges of the bag comprise a pair of complementary sealing strips which permit secure closure. The exterior of the bag is imprinted with both a scale indicative of the volume of fluid collected and an opaque white strip onto which needed information may be written. The sheet plastic of which the bag is formed may be either clear for general medical application to permit ease of inspection or opaque in the case of aircraft use.

The bag of the invention furthermore includes a "duck-bill" type valve, as previously described, and which is sealed to a lower portion of the funnel to prevent the bag's contents from minor spills before the sealing strips securely seal the bag closed.

DETAILED DESCRIPTION OF THE INVENTION AND PREFERRED EMBODIMENTS THEREOF

Figure 1:
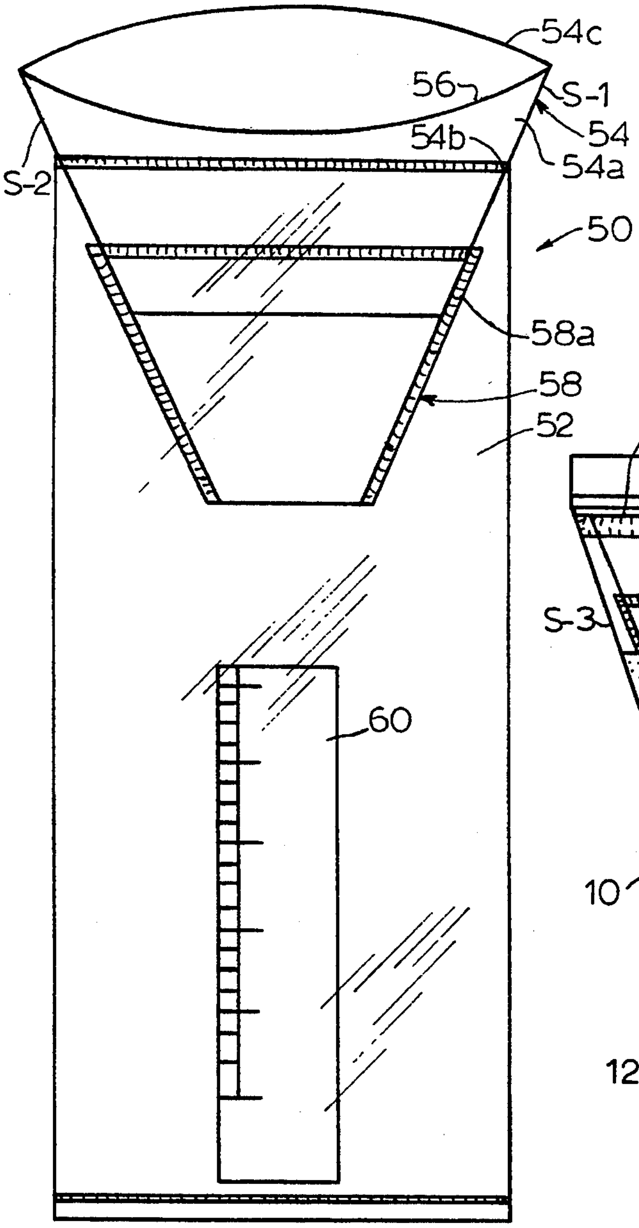
FIG. 1 (PRIOR ART)
FIG. 1 is a front elevation view of a body fluid collection bag of the prior art with the bag being illustrated as it appears as viewed in elevation when folded flat.

A disposable body fluid collection bag 50 of the prior art is illustrated in FIG. 1 as a clear plastic bag 52 of rectangular shape when folded flat and viewed in elevation. See for reference the previously referred to U.S. Pat. 3,797,734. Funnel 54 includes an upper portion 54*a* formed of a relatively resiliently flexible, foldable, waterproofed paperboard like material and whose external periphery 54*b* is sealingly attached to the upper open end of bag 50 so as to cause funnel 54 to reside partially within and partially above the upper open end of the bag 50. The upper portion 54a of funnel 54 is formed with a pair of downwardly curved, parallel fold lines 56 on opposite surfaces thereof only one of such score lines being shown in FIG. 1. Funnel 54 is opened by pressing on the opposite side edges S-1, S-2. Upper edge 54c appears as being upwardly curved in the flat condition of FIG. 1. When funnel 54 is fully opened, the upper peripheral edge 54c of funnel 54 occupies a substantial horizontal plane and forms an opening which is circular in transverse cross section. At the lower portion of funnel 54 is "duck-bill" valve 58, adapted to prevent minor spills of contained fluid. Duck-bill valve 58 forms a continuation of funnel 54 and comprises an inverted truncated cone shaped plastic tube located within bag 50 and having its upper edge 58a encircling and sealed to the outer surface of the lower portion of funnel 54. As the fluid passes funnel 54 and through "duck-bill" valve 58, the inner walls of valve 58 become wet. When fluid is no longer entering valve 58 from above, the sides thereof tend to re-close and the wetness on the surface causes the sides to lightly adhere to each other. If the fluid in the bag thereafter for any reason tends to move toward the funnel 14, valve 58 obstructs the flow, unless the pressure applied to valve 58 is excessive, such as may occur if the bag is inverted or squeezed. A printed scale 60, such as previously used in the EMS type bag, is shown on the side of the prior art bag 50 so as to afford a ready means of measuring the volume of fluid collected.

Figure 2:
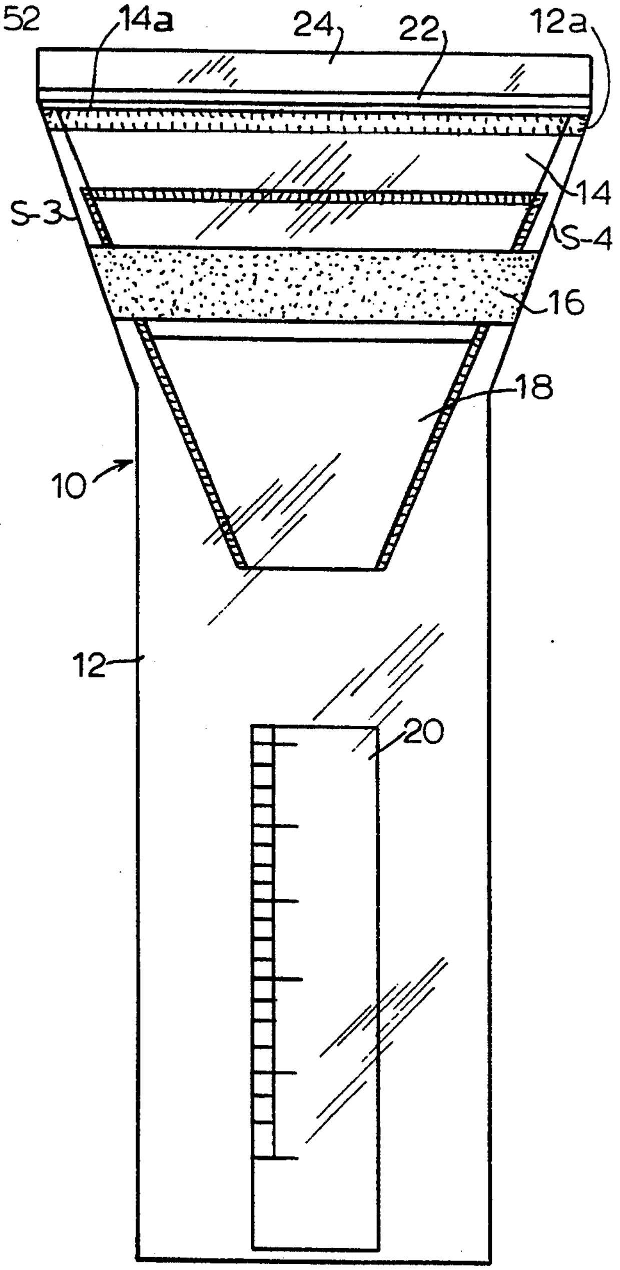
FIG. 2 is a front elevation view of a body fluid collection bag according to a first embodiment of the present invention with the bag being illustrated as it appears as viewed in elevation when folded flat.
Figure 3:
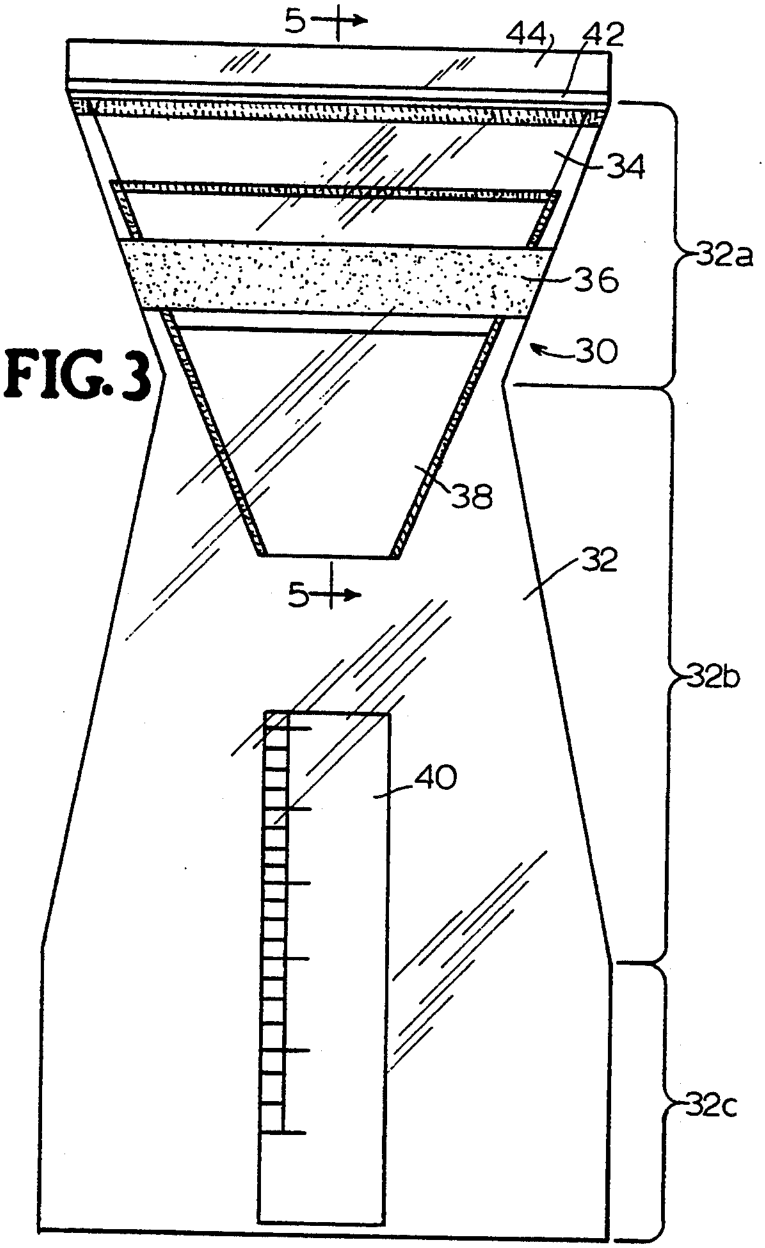
FIG. 3 is a front elevation view of a body fluid collection bag as viewed when folded flat according to a second embodiment of the present invention.
Figure 4:
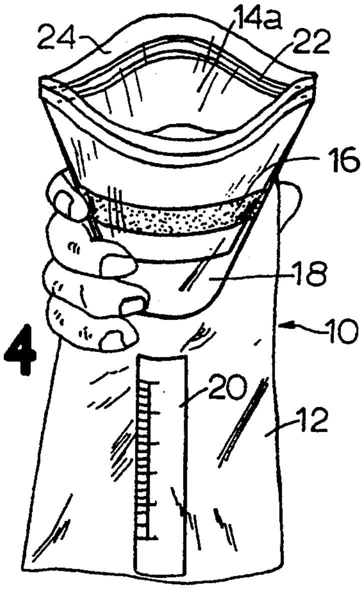
FIG. 4 is a perspective view of the first embodiment body fluid collection bag of the invention as it appears when being held open ready for use.

FIGS. 2-5 are illustrative of the bag configuration and improved sealing means of the invention as seen in two embodiments of different shape. FIG. 2 discloses a disposable bag 10 having a collecting bag 12 having an upper end 12a whose inner surface is sealingly attached to and completely encloses the upper edge 14a of funnel 14 and which appears as a generally horizontal edge in the flat condition of FIG. 2. Funnel 14 is formed of the relatively resiliently flexible, waterproofed paperboard like material described above. The upper portion of collection bag 12 is formed in an inverted truncated cone like shape to follow generally the, contour of funnel 14 and further to enhance the manipulation characteristics when the user holds bag 12 and compresses the side portions S-3, S-4, of funnel 14 to open funnel 14 as shown in FIG. 4. At the lower portion of funnel 14, and within collection bag 12, a duck-bill type valve 18 is sealed to the outer surface and lower portion of funnel 14. From the description given, it will be appreciated that funnel 14 as well as valve 18 reside entirely within the bag 12 and that valve 18 effectively forms a continuation of funnel 14.

As is known in the art, valve 18, in the form of a "duck-bill" valve, is formed of a flexible plastic sheet as explained above and functions to prevent escape of small quantities of fluid from the interior of collection bag 12. Since it is anticipated that the quantity of body fluid will reach a certain height in collecting bag 12, the lower termination of valve 18 is positioned at a height greater than the likely maximum fluid height. A fluid measuring volume gauge 20, as is known, is printed on the side of the plastic sheet formed collecting bag 12. For uses in other than a hospital or clinical setting, it is anticipated that volume gauge 20 will not be included.

Collecting bag 12 terminates at its open upper end a distance above the upper end of funnel 14 with a pair of closure lips 24, which comprise integrally formed, complementarily opposed, seal strips 22. Seal strips 22 may be of any convenient form, and are preferably of a substantially tightly interlocking channel and vane extrusion configuration known to seal plastic bags for household use and provide a substantially fluid tight seal such as for sandwich bags and the like. The addition of such interlocking strip seals 22 on portions of bag 12 extending above funnel 14 provides a secure sealing means able, when closed, to prevent fluid loss even if the bag is inverted or squeezed with moderate pressure. In cooperation with the sealing effect of the duck-bill valve 18, it can be seen that a substantially improved sealing construction is obtained.

An opaque portion 16, preferably of a light color and having a non-slippery surface to facilitate writing of identifying information, is printed or otherwise formed at an appropriate position on the exterior of disposable bag 10. Opaque printed portion 16 may be of any convenient shape and may also be further printed in a contrasting color to a light background color with suggestive terms, such as, for example, "name" and "date".

Disposable bag 10, and in particular funnel 14, as shown being squeezed into an open position in FIG. 4, by the hand of a user, is adapted to receive body fluids, including vomit and urine. By forming upper edge 14a of funnel 14 as a relatively straight horizontal edge as viewed in the flat condition of FIG. 2, where funnel 14 is ,Dressed on the sides and opened as viewed in FIG. 4, the edges 14a tend to advantageously curve downwardly to better fit the user. Upon release, the walls of funnel 14 because of their shape and inherent resiliency lend to relax and come together. At this stage with the bag full, the seal strips 22 may be tightly pressed together to form a fluid tight seal.

A variation on the shape of the disposable bag 30 of the invention is illustrated as a second embodiment in FIG. 3. In particular, collecting bag 32 is shaped so as to have, when filled, an upper outwardly tapered portion 32a, an intermediate inwardly tapered portion 32b and a substantially cylindrical lower portion 32c. The configuration of funnel 34, lips 44, duck-bill valve 38 and strip seal 42 are similar to those described above in relation to the bag 10 illustrated in FIG. 2. Due to the variation in diameter occasioned by the shape of the tapering collection bag 32, the values attached to volume gauge 40 will differ from the substantially linear relationship which would suffice in a parallel-sided bag as disclosed above.

Figure 5:
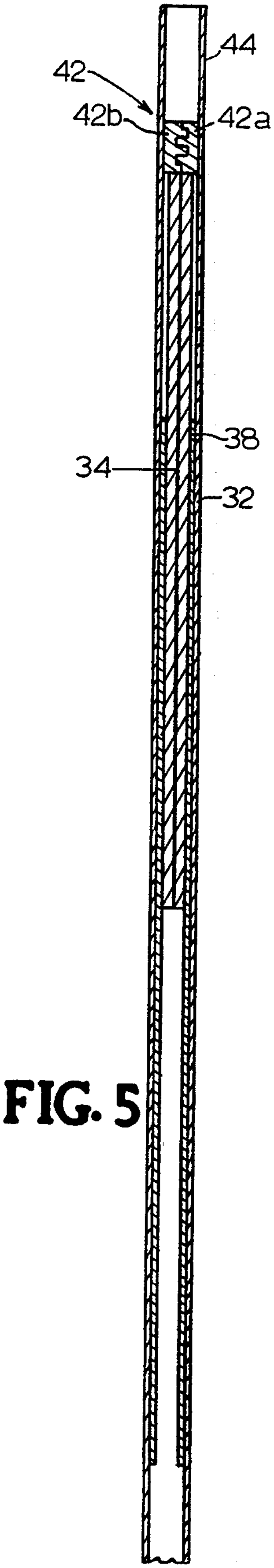
FIG. 5 is a cross sectional view taken in the direction of line 5—5 of FIG. 3 and enlarged for clarity.

The cross section of disposable bag 30, as taken in the direction of line 5—5 of FIG. 3 is seen in FIG. 5. As described in sequence from the exterior to the interior, collection bag 32 surrounds valve 38, the inner top surface of bad 32 is sealed to the outer top surface of funnel 34 and the inner top surface of valve 38 is sealed to the lower outer surface of funnel 34. Lips 44 and seal strip 42, comprising vane component 42a and channel component 42b are seen at the upper end of collection bag 32.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A disposable device for collection of body fluids, comprising:

(a) a body fluid collection bag formed of a flexible material, having an open topper upper portion in the shape when flat of a trapezoid having a top edge longer than a bottom edge, and having a closed bottom lower portion contiguous with said upper portion;

(b) first and second complementary seal strips integrally formed on and extending across respective opposed inner surfaces of said upper portion and being located parallel to and immediately below said top edge;

(c) a funnel formed of a resilient material, shaped to conform substantially to the shape of said upper portion of said bag, and having an outer surface of said funnel sealed to an inner surface of said upper portion of said bag in a location so that said funnel resides immediately beneath said complementary seal strips;

(d) a flexible non-return valve formed of a flexible material and having two opposed side walls connected at respective side edges thereof and having an upper edge and lower edge and with an inner surface of said upper edge sealed to an ,outer surface of said funnel and said lower edge residing below a bottom edge of said funnel;

(e) a scale formed on said lower portion of said bag and adapted to allow measurement of a quantity of body fluid collected in said bag; and (f) a marking surface formed on said bag and adapted to received inscription of identification information relating to said collected body fluid.

2. The disposable device according to claim 1, wherein said first seal strip is formed as a channel and said second seal strip is formed as a vane adapted to releasably interlock in sealing relation with said channel.

* * * * *

UNITED STATES PATENT AND TRADEMARK OFFICE

CERTIFICATE OF CORRECTION

PATENT NO. : 5,356,398

DATED : October 18, 1994

INVENTOR(S) : Michael W. Willis

It is certified that error appears in the above-indentified patent and that said Letters Patent is hereby corrected as shown below:

Column 1, line 22, correct "a" to read --as--.

Column 1, line 59, correct "form" to read --from--.

Column 1, line 60, correct "know" to read --known--.

Column 2, line 4, after "collection", insert --of--.

Column 2, line 9, delete both commas.

Column 3, line 41, delete comma.

Column 4, line 26, delete comma, first occurance; and correct "Dressed" to read --pressed--.

Column 4, line 50, correct "bad" to read --bag--.

Column 4, line 67, correct "topper" to read --topped--.

Column 6, line 3, delete comma.

Signed and Sealed this

Twenty-seventh Day of December, 1994

Attest:

BRUCE LEHMAN

Attesting Officer

*Commissioner of Patents and Trademarks*